(12) United States Patent
An et al.

(10) Patent No.: US 10,328,282 B2
(45) Date of Patent: Jun. 25, 2019

(54) SYSTEM AND METHOD FOR NOVEL CHANCE-CONSTRAINED OPTIMIZATION IN INTENSITY-MODULATED PROTON THERAPY PLANNING TO ACCOUNT FOR RANGE AND PATIENT SETUP UNCERTAINTIES

(71) Applicants: Yu An, Phoenix, AZ (US); Jianming Liang, Scottsdale, AZ (US); Wei Liu, Scottsdale, AZ (US)

(72) Inventors: Yu An, Phoenix, AZ (US); Jianming Liang, Scottsdale, AZ (US); Wei Liu, Scottsdale, AZ (US)

(73) Assignees: Mayo Foundation for Medical Education and Research, Rochester, MN (US); Arizona Board of Regents on behalf of Arizona State University, Scottsdale, AZ (US)

( * ) Notice: Subject to any disclaimer, the term of this patent is extended or adjusted under 35 U.S.C. 154(b) by 75 days.

(21) Appl. No.: 15/209,699

(22) Filed: Jul. 13, 2016

(65) Prior Publication Data
US 2017/0014642 A1    Jan. 19, 2017

Related U.S. Application Data

(60) Provisional application No. 62/192,038, filed on Jul. 13, 2015.

(51) Int. Cl.
*A61N 5/10* (2006.01)

(52) U.S. Cl.
CPC ......... *A61N 5/1039* (2013.01); *A61N 5/1084* (2013.01); *A61N 2005/1087* (2013.01)

(58) Field of Classification Search
CPC ............... A61N 5/1039; A61N 5/1084; A61N 2005/1087
See application file for complete search history.

(56) References Cited

U.S. PATENT DOCUMENTS

2013/0217948 A1 * 8/2013 Mihaylov ............ A61N 5/1031
                                                              600/1

OTHER PUBLICATIONS

Liu, et al. PTVbased IMPT optimization incorporating planning risk volumes vs robust optimization. Medical Physics 2013;40(2):021709-021708.

(Continued)

*Primary Examiner* — Christine H Matthews
*Assistant Examiner* — Joshua Daryl D Lannu
(74) *Attorney, Agent, or Firm* — Quarles & Brady LLP

(57) ABSTRACT

A system and methods are provided for generating intensity modulated proton therapy plans robust to various kinds of delivery uncertainties with the capability for treatment planners to control the balance between plan quality and robustness. The system obtains a representation of a subject and a proton beam configuration that describes a number of beamlets and their respective arrangement. The system computes an objective function, in the treatment planning system, first part of which is about dose deviations from the prescribed dose in the target volumes, second part of which is about dose deviations from the dose constraint in the non-target volumes, and computing dose volume constraints for targets using a probability to control the dose distribution in the target volumes to be between a lower threshold and an upper threshold. Based on this information, the system obtains a robust chance-constrained treatment planning model with a user-adjustable tolerance level.

20 Claims, 8 Drawing Sheets

(56) References Cited

OTHER PUBLICATIONS

Liu, et al. Dosimetric benefits of robust treatment planning for intensity modulated proton therapy for base-of-skull cancers. Practical Radiation Oncology 2014;4(6):384-391.

Liu, et al. Exploratory study of 4d versus 3d robust optimization in intensitymodulated proton therapy for lung cancer. International Journal of Radiation Oncology* Biology* Physics 2015.

Li, et al. Beyond gaussians: a study of single-spot modeling for scanning proton dose calculation. Physics in Medicine and Biology 2012;57(4):983.

Lim, et al. Recent advances in intensity modulated proton therapy treatment planning optimization. In: Proceedings of the 15th Asia Pacific Industrial Engineering and Management Systems Conference, pp. 1520-1525, Jeju, Korea. 2014.

Lomax. Intensity modulated proton therapy and its sensitivity to treatment uncertainties 1: the potential effects of calculational uncertainties. Physics in Medicine and Biology 2008;53(4):1027.

Lomax. Intensity modulated proton therapy and its sensitivity to treatment uncertainties 2: the potential effects of inter-fraction and inter-field motions. Physics in Medicine and Biology 2008;53(4):1043.

Lomax, et al. Intensity modulated proton therapy: a clinical example. Medical Physics 2001;28(3):317-324.

Pflugfelder, et al. Worst case optimization: a method to account for uncertainties in the optimization of intensity modulated proton therapy. Physics in Medicine and Biology 2008;53(6):1689.

Unkelbach. et al. Reducing the sensitivity of IMPT treatment plans to setup errors and range uncertainties via probabilistic treatment planning. Medical Physics 2009;36(1):149-163.

Unkelbach, et al. Accounting for range uncertainties in the optimization of intensity modulated proton therapy. Physics in Medicine and Biology 2007;52(10):2755.

Unkelbach, et al. Range, setup and dose calculation errors in IMPT and their interrelation. In: World Congress on Medical Physics and Biomedical Engineering, Sep. 7-12, 2009, Munich, Germany. Springer; 2009, p. 900-903.

Liu, et al. Robust optimization of intensity modulated proton therapy. Medical Physics 2012;39(2):1079-1091.

Verellen, et al. Innovations in image-guided radiotherapy. Nature Reviews Cancer 2007;7(12):949-960.

Van Herk, et al. Inclusion of geometric uncertainties in treatment plan evaluation. International Journal of Radiation Oncology Biology Physics 2002;52(5):1407-1422.

Bortfeld, et al. Effects of intra-fractionmotion on IMRT dose delivery: statistical analysis and simulation. Physics in Medicine and Biology 2002;47(13):2203.

Register, et al. Proton stereotactic body radiation therapy for clinically challenging cases of centrally and superiorly located stage i non-small-cell lung cancer. International Journal of Radiation Oncology* Biology* Physics 2011;80(4):1015-1022.

Kang, et al. 4d proton treatment planning strategy for mobile lung tumors. International Journal of Radiation Oncology* Biology* Physics 2007;67(3):906-914.

Zhang, et al. Intensity-modulated proton therapy reduces the dose to normal tissue compared with intensity-modulated radiation therapy or passive scattering proton therapy and enables individualized radical radiotherapy for extensive stage iiib non-small-cell lung cancer: a virtual clinical study. International Journal of Radiation Oncology* Biology* Physics 2010;77(2):357-366.

Jiang, et al. An experimental investigation on intra-fractional organ motion effects in lung IMRT treatments. Physics in Medicine and Biology 2003;48(12):1773.

Chan, et at. A robust approach to IMRT optimization. Physics in Medicine and Biology 2006;51(10):2567.

Fredriksson, et al. Minimax optimization for handling range and setup uncertainties in proton therapy. Medical Physics 2011;38(3):1672-1684.

Liu, et al. Effectiveness of robust optimization in intensity-modulated proton therapy planning for head and neck cancers. Medical Physics 2013;40(5):051711-051718.

Liu, et al. Influence of robust optimization in intensity-modulated proton therapy with different dose delivery techniques. Medical Physics 2012;39(6):3089-3101.

Liu, et al. Impact of respiratory motion on worst-case scenario optimized intensity modulated proton therapy for lung cancers. Practical Radiation Oncology 2015;5(2):e77-e86.

Chen, et al. Including robustness in multi-criteria optimization for intensity-modulated proton therapy. Physics in Medicine and Biology 2012;57(3):591.

Fredriksson. A characterization of robust radiation therapy treatment planning methods—from expected value to worst case optimization. Medical Physics 2012;39(8):5169-5181.

Pr'ekopa. Probabilistic programming. Handbooks in Operations Research and Management Science 2003;10:267-351.

Romeijn, et al. A new linear programming approach to radiation therapy treatment planning problems. Operations Research 2006;54(2):201-216.

Chan, et al. A robust-cvar optimization approach with application to breast cancer therapy. European Journal of Operational Research 2014;238(3):876-885.

Trofimov, et al. Evaluation of dosimetric gain and uncertainties in proton therapy delivery with scanned pencil beam in treatment of base-of-skull and spinal tumors. International Journal of Radiation Oncology* Biology* Physics 2010;78(3):S133-S134.

Geoffrion. Generalized benders decomposition. Journal of Optimization Theory and Applications 1972;10(4):237-260.

Zeng, et al. Chance constrained mixed integer program: bilinear and linear formulations, and benders decomposition. Submitted 2014.

* cited by examiner

SYSTEM AND METHOD FOR NOVEL CHANCE-CONSTRAINED OPTIMIZATION IN INTENSITY-MODULATED PROTON THERAPY PLANNING TO ACCOUNT FOR RANGE AND PATIENT SETUP UNCERTAINTIES

CROSS-REFERENCE TO RELATED APPLICATIONS

This application claims the benefit of U.S. Provisional Patent Application Ser. No. 62/192,038, filed on Jul. 13, 2015, and entitled "System And Method For Novel Chance-Constrained Optimization in Intensity-Modulated Proton Therapy Planning to Account for Range and Patient Setup Uncertainties."

STATEMENT REGARDING FEDERALLY SPONSORED RESEARCH

This invention was made with government support under CA168984 awarded by the National Institutes of Health. The government has certain rights in the invention.

BACKGROUND

The field of the disclosure relates to systems and methods for ionizing radiation treatment. More particularly, the disclosure relates to systems and methods for intensity modulated proton therapy.

Lung cancer is the leading cancer killer worldwide, and about 30% to 40% of patients with locally advanced lung cancer require combined-modality treatment, including radiotherapy. However, with photon radiotherapy and concurrent chemotherapy, the 5-year survival is only about 15% for patients with stage III non-small cell lung cancer. Among those, about 50% experience local disease recurrence. Also, uncontrolled local disease may continue to seed to distant organs, resulting in distant metastasis and death. Hence, further improvements in survival of patients suffering from lung, and other types of cancer, require the safe delivery of higher radiation doses, which is not possible with photon radiotherapy.

Proton therapy approaches take advantage of the energy deposition profile of protons in tissue to provide highly conformal exposure of tumors while sparing organs-at-risk ("OAR"). Specifically, protons have a finite penetration depth in dependence of their energy, and the radiation dose delivered is maximum within a short distance of a proton's range, known as the Bragg peak. In particular, tissues located closer to the surface of a body receive less radiation dose compared to those at the Bragg peak. In addition, the dose profile drops dramatically beyond the Bragg peak, and hence tissues therein receive practically no radiation dose. As such, proton treatment systems make use of the dose deposition characteristics of protons in order to maximize tumor tissue coverage while minimizing dose to normal tissues as much as possible.

Unlike passive-scattering proton therapy ("PSPT") techniques, which includes scattering materials placed along the path of protons in order to provide lateral field sizes and depth of coverage useful for clinical applications, intensity-modulated proton therapy ("IMPT") uses magnetic steering of narrow proton beams, know as a beamlets, to deliver radiation dose to treatment target. Specifically, the energies and intensities of many individual beamlets, typically aimed at a target from multiple directions, are optimized using sophisticated computer algorithms that implement mathematically specified criteria, captured in what is known as an objective function. In the treatment of lung tumors, for example, this approach offers improved high-dose conformality when compared with PSPT, with better healthy tissue sparing in the mid- to low-dose range. Using such an objective function, an optimal compromise between adequate tumoricidal dose to a target and sparing of critical normal structures is achieved.

Several factors are known to change the dose received by target and normal structures as compared to the planned dose, thereby compromising the safety and efficacy of the treatment. For instance, inter-fractional variation in patient geometry, caused by tumor shrinkage, patient weight change, setup variation, proton range uncertainty, and so on, can cause significant differences in delivered dose distributions. Specifically, patient setup uncertainties can occur through the course of simulation and daily treatment. In addition, proton range uncertainty caused by tumor shrinkage, patient weight change, and computed tomography ("CT") number and stopping power ratio uncertainties may significantly alter dose to target and surrounding healthy, or non-target tissues. Unlike uncertainties caused by respiratory motion, patient setup and range uncertainties include systematic uncertainties that can affect the delivery of an intended dose throughout the course of multi-fractionated treatment.

Generally, for intensity-modulated radiotherapy ("IMRT") approaches that provide treatment using photons, setup uncertainties are typically taken into account by adding isotropic margins to a clinical target volume ("CTV"), which reflects gross tumor and microscopic disease, to form a planning target volume ("PTV"). On the other hand, in PSPT, range and setup uncertainties are typically handled by adding lateral margins for setup uncertainties around the CTV and distal and proximal margins to account for range uncertainties. The PTV margin is chosen with the implicit assumption that the CTV will remain covered with the prescribed isodose surface with high probability (e.g., 95%) in the presence of the above described uncertainties. This is generally a good assumption for photons because the spatial distributions of photon dose are minimally perturbed by uncertainties. However, such approach of margin expansion may not be effective in IMPT due to the highly fluctuating nature of beamlet intensities and the resulting inhomogeneous dose distributions per beam in the target volume. Nevertheless, in the absence of suitable alternatives to assigning margins, the current practice in IMPT is to expand GTV to internal GTV and expand the CTV/ITV to form a PTV in a manner similar to the practice for photon therapy. As a result, the produced dose distributions are deficient in robustness and may cause IMPT dose distributions delivered to the patient to be significantly different from those prescribed, leading to unforeseen clinical consequences.

In light of the above, there is a need for systems and methods directed producing treatment plans amenable to the influence of uncertainties.

SUMMARY OF THE DISCLOSURE

The present disclosure overcomes the aforementioned drawbacks by providing a system and method that adopts a probabilistic framework (chance-constrained optimization) in IMPT planning to hedge against the influence of uncertainties.

In one aspect of the present disclosure, a method for generating intensity modulated proton therapy plans is provided. The method includes obtaining, by a treatment planning system, a representation of a subject that includes information related to target and non-target volumes of interest, obtaining, by the treatment planning system, a proton beam configuration that describes a number of beamlets and their respective arrangement, and obtaining, by the treatment planning system, a target dose distribution model in the target volumes, prescribed doses for the target volumes, and doses constraint in the non-target volumes. The method also includes computing an objective function, using the treatment planning system, the objective function having a first part with dose deviations from the prescribed doses in the target volumes, a second part with dose deviations from the dose constraints in the non-target volumes, and computing dose volume constraints for targets using a probability controlling a dose distribution in the target volumes between a lower threshold and an upper threshold. The method further includes optimizing the objective function with the treatment planning system to determine a set of intensity weights for each beamlet in the proton beam configuration, wherein the objective function is calculated using the first part and second part and the dose volume constraints, and generating a treatment plan with the treatment planning system using the intensity weights determined by optimizing the objective function.

In another aspect of the present disclosure, a system for generating intensity modulated proton therapy plans is provided. The system includes an input configured to accept a representation of a subject that includes information related to target and non-target volumes of interest. The system also includes at least one processor configured to obtain a target dose distribution model in the target volumes, prescribed doses of the target volumes, and dose constraints in the non-target volumes, compute an objective function, using the treatment planning system, the objective function having a first part with dose deviations from the prescribed doses in the target volumes, a second part with dose deviations from the dose constraints in the non-target volumes, and computing dose volume constraints for targets using a probability controlling a dose distribution in the target volumes between a lower threshold and an upper threshold. The at least one processor is also configured to generate the treatment plan by optimizing the objective function to determine a set of intensity weights for each beamlet in the proton beam configuration.

In yet another aspect of the present disclosure, a method for generating intensity modulated proton therapy plans is provided. The method includes obtaining, by a treatment planning system, a representation of a subject that includes information related to target and non-target volumes of interest (VOIs), obtaining, by the treatment planning system, a proton beam configuration that describes a number of beamlets and their respective arrangement, and obtaining, by the treatment planning system, a target dose distribution model in the target VOIs, prescribed doses for the target VOIs, and dose constraints for the non-target VOIs. The method also includes computing dose volume constraints for the target VOIs using a selectable parameter controlling a probability for a dose distribution in the target VOIs to be between a lower threshold and an upper threshold, and optimizing an objective function with the treatment planning system to determine a set of intensity weights for each beamlet in the proton beam configuration, wherein the objective function is calculated using dose deviations from the prescribed doses in the target VOIs, dose deviations from the dose constraints in the non-target VOIs, and the dose volume constraints for the target VOIs. The method further includes generating a treatment plan with the treatment planning system using the intensity weights determined by optimizing the objective function.

The foregoing and other aspects and advantages of the disclosure will appear from the following description. In the description, reference is made to the accompanying drawings which form a part hereof, and in which there is shown by way of illustration a preferred embodiment of the disclosure. Such embodiment does not necessarily represent the full scope of the disclosure, however, and reference is made therefore to the claims and herein for interpreting the scope of the disclosure.

DETAILED DESCRIPTION OF THE DISCLOSURE

Figure 1:
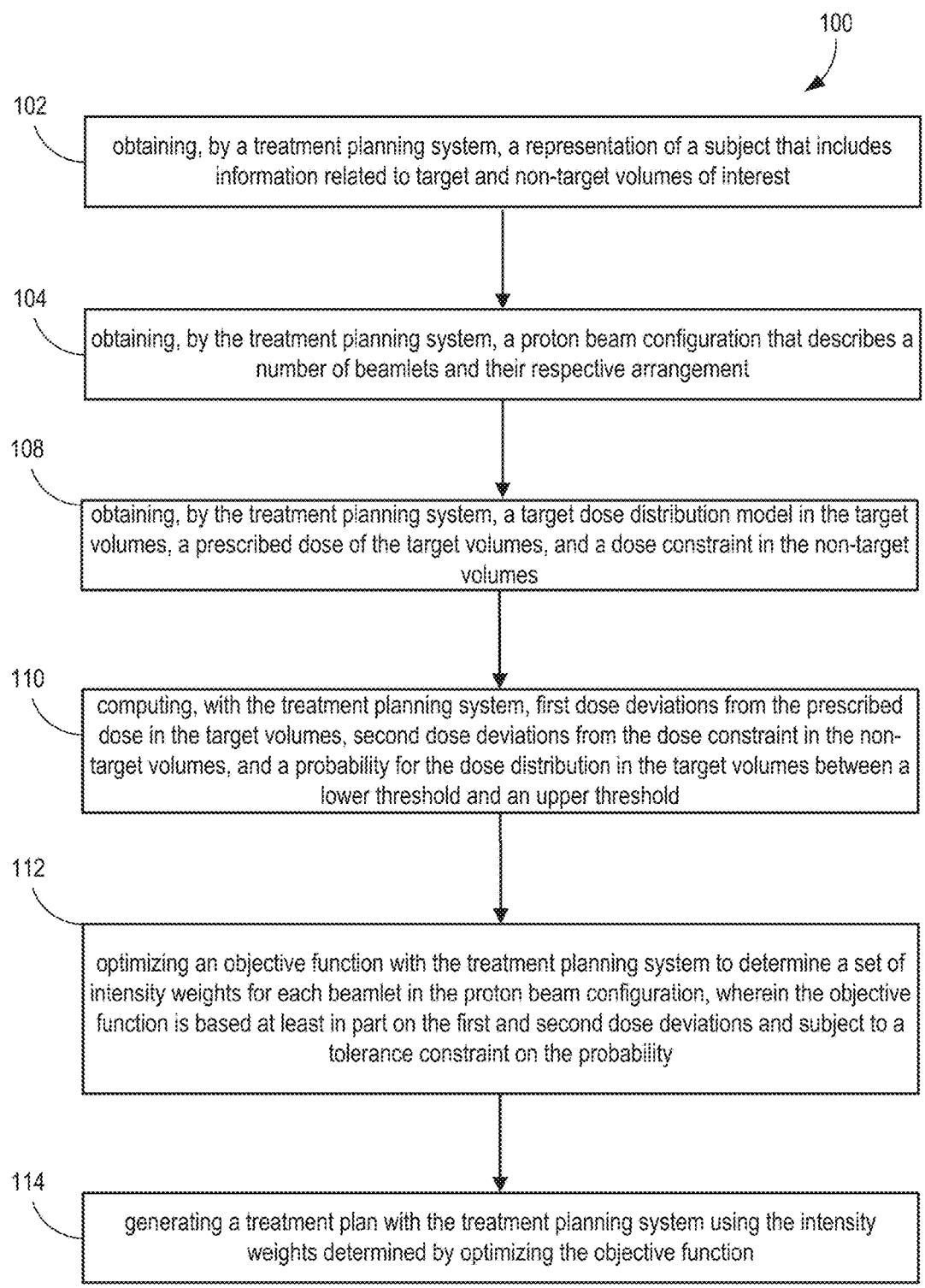
FIG. 1 is a flowchart setting forth the steps of an exemplary proton treatment planning method in accordance with the present disclosure.

Intensity-modulated proton therapy ("IMPT") is an advanced form of proton therapy that can achieve highly conformal tumor dose coverage and superior sparing of organs at risk ("OARs"). However, IMPT is highly sensitive to uncertainties, including patient setup, proton range in tissue, respiratory motion, tumor shrinkage, weight loss and so on. As a result, the dose distributions provided by conventional treatment planning systems may differ significantly from the dose distribution delivered within the patient, leading to unforeseen clinical consequences. To derive the highest clinical benefit, it is therefore important to mitigate the influence of uncertainties in the plan generation process in order to deliver particle therapy precisely and predictably.

In order to address uncertainties, different optimization methods have been proposed. Although such optimization methods have been shown to be effective in rendering IMPT plans less sensitive to some uncertainties, in many cases it may be desirable for treatment planners to control the tradeoff between plan robustness and normal tissue sparing. For example, one proposed method is based on fluence map optimization (FMO) that focuses on finding optimal beamlet intensities given beam angles and influence matrix, which records dose contributions from each beamlet of unit intensity to each voxel. The objective of FMO is to deliver the prescribed dose to the tumor while minimizing doses delivered to OARs. Deterministic FMO models, however, do not consider range uncertainties, organ motions, and patient setup uncertainties, may produce IMPT plans that are not robust and hence the treatment quality may deteriorate during the beam delivery, resulting in undesired clinical consequence.

Therefore, the present disclosure provides a novel framework for use in IMPT that addresses the shortcomings previous technologies, namely, a robust conditional value at risk ("CVaR") chance-constrained treatment optimization. In particular, the present approach can proactively assure plan quality under various uncertainty scenarios, and provides a tool for treatment planners to actively control the balance between plan robustness and nominal plan quality. The provided system and method may therefore generate IMPT plans that are robust to various uncertainties, such range uncertainty and patient setup uncertainty, and include the capability for treatment planners to control the balance between plan quality and robustness.

As will be described, a representation of a subject and a proton beam configuration that describes a number of beamlets and their respective arrangement, may be obtained. An objective function may then be computed, the objective function including dose deviations from prescribed doses in the target volumes, and dose deviations from dose constraints in the non-target volumes. In addition, the objective function includes dose volume constraints for targets using a probability to control the dose distribution in target volumes to values between a lower threshold and an upper threshold. Based on this information, a robust chance-constrained treatment planning model may be obtained having a selectable or user-adjustable tolerance level. In some aspects, the model can be reformulated into a tractable mixed-integer programming problem and may be further sped up using Benders decomposition. With explicit control of plan robustness, the chance-constrained robust optimization model can be used to generate superior IMPT plans compared to conventional methods.

Turning to FIG. 1, a flowchart is shown setting forth the steps of an example method for proton treatment planning in accordance with the present disclosure. The process 100 may begin at process block 102, whereby a representation of a subject is obtained by a treatment planning system. The representation of a subject includes information related to target and non-target volumes of interest. The representation may include any number of images acquired from a subject, including images acquired during a treatment simulation protocol. For example, such images may be acquired using a number of imaging modalities, including computed tomography ("CT"), magnetic resonance ("MR"), positron emission tomography ("PET"), proton CT, and other imaging modalities, which may provide temporal information as well. In addition, the representation may also include information related to target and non-target volumes of interest ("VOI"). This may include contours of diseased and normal tissue structures, which may be identified by a clinician, or as a result of an applied segmentation algorithm.

A common strategy in IMPT optimization for generating treatment plans involves first computing dose contributions per unit intensity of all proton beamlets associated with the radiation treatment to each voxel in a VOI, which may include both target and critical structures, prior to optimization. Such computations, which can be performed using any appropriate pencil-beam algorithm, are captured in what is known as an influence matrix ("IM"). These computations allow for the separation of complex dose calculations from the optimization process. Subsequently, during optimization, weights are determined in accordance with desired clinical objectives, in order to determine optimized dose distributions. This approach has the advantage of speed and efficiency since the actual dose distribution can be updated quickly using the IM.

In this manner, at process block 104, the treatment planning system can obtain a proton beam configuration that describes a number of beamlets and their respective arrangement. The beam configuration may be stored in a computer memory accessible to the treatment planning system. In some aspects, the beam configuration may selected or adapted by a clinician based on clinical protocols or needs. A number of dose distributions may then be computed based on multiple uncertainty scenarios. In particular, using a representation of the subject, as described, and a prescribed, or determined, proton beam configuration that describes a number of proton beamlets and their respective arrangement relative to the subject, multiple dose distributions may be calculated. In some aspects, at process block 104, uncertainty scenarios may include inter-fractional setup uncertainties. For instance, setup uncertainties may be considered to be random and may be modeled by calculating the dose distribution for any respiratory phase by shifting the isocenter of a patient's CT image in antero-posterior ("AP"), superior-inferior ("SI"), and lateral, or right-left, ("RL") directions by any margins, such as, margins commonly used for defining a planning target volume ("PTV"). This yields 6 dose distributions plus 1 nominal dose distribution and the corresponding IMs.

Other uncertainty scenarios may include proton range uncertainties. Specifically, proton range uncertainties for each patient can be generally systematic and propagate through the whole course of the treatment, but they are usually random for a patient population. As such, they may be modeled by calculating dose distribution for any respiratory phase by scaling stopping power ratios by say, $-3.5\%$ and $+3.5\%$, although other values are possible, to generate dose distributions and IMs corresponding to maximum and minimum proton ranges, respectively.

The above-described example uncertainty scenarios, including dose distributions for nominal, minimum, and maximum proton ranges, as well as dose distributions whereby the isocenter of the patient from the nominal position is rigidly shifted in the AP, SI, and RL directions, respectively, result in 21 dose distributions (7 per proton range). However, any number dose distributions may be computed in dependence of a desired number of uncertainty scenarios.

At process block 106, the treatment planning system obtains a target dose distribution model in the target volumes, a prescribed dose of the target volumes, and a dose constraint in the non-target volumes. The treatment planning system may obtain the target dose distribution model based on historical patient data. For example, the treatment planning system may first select a probability model and then use historical data to determine the variance for the probability model. The prescribed dose of the target volumes and the dose constraint in the non-target volumes may be obtained based on a user input from a user interface. The treatment planning system may receive a tolerance level $\varepsilon$ from a user interface and setting a threshold level to be $1-\varepsilon$, where chance constraint on the probability ensures that the probability is not less than the threshold level.

At process block 108, the treatment planning system computes first dose deviations from prescribed doses in the target volumes, second dose deviations from the dose constraints in the non-target volumes, and a probability for the dose distribution in the target volumes to be between a lower threshold and an upper threshold. In some implementations, this probability can be adjusted by the treatment planners prior to optimization using a selectable parameter. For example, the first dose deviations from the prescribed dose in target volumes may be computed using $$\sum_{t \in T} \frac{\alpha_t}{|CTV_t|} \sum_{i \in CTV_t} |D_{ti}(\omega_0) - D_t^0|.$$

The second dose deviations from the dose constraint in the non-target volumes may be computed using $$\sum_{n \in O} \frac{\alpha_n}{|V_n|} \sum_{i \in V_n} (D_{ni}(\omega_0) - D_n^0)^+.$$

For example, in IMPT, tumors are irradiated by multiple beams incident from various angles. Hereafter, the set of all tumors is denoted by T and that of all OARs by 0. Every beam can be decomposed into many small beamlets. The set of all beamlets in all beams is denoted by J. In addition, all tumors and OARs are discretized into sets of voxels. $CTV_t$ is used to denote the set of all voxels in the CTV of tumor t in T. $V_n$ is the set of all voxels of the OAR n in 0. Prescription dose of the tumor t and dose constraint of OAR n are represented by $D_t^0$ and $D_n^0$, respectively. The dose received by voxel i of tumor t is denoted by $D_{ti}$ and that received by voxel i of OAR n by $D_{ni}$. The intensity of each beamlet $j \in J$, $d_j$, is the decision variable. In the influence matrix, its element $k_{ij}$ is the dose contribution of the beamlet j of unit intensity at voxel i. Therefore, $D_{ti}$ and $D_{ni}$ are calculated using the equations $D_{ti} = \sum_{j \in J} k_{ij} d_j$ and $D_{ni} = \sum_{j \in J} k_{ij} d_j$.

Various uncertainties, including range and setup uncertainties, may perturb the influence matrix and hence the dose. Let $\Omega$ be the set of all possible uncertainty scenarios. $\omega_0$ stands for the nominal scenario. In uncertainty scenario $\omega \in \Omega$, $D_{ti}(\omega)$ and $D_{ni}(\omega)$ are the doses corresponding to uncertainty scenario $\omega$. Let $f_t(d)$ and $f_n(d)$ be the parameters describing dose distributions of tumor t and OAR n, respectively. Correspondingly, $f_t(d,\omega)$ and $f_n(d,\omega)$ are the values of $f_t(d)$ and $f_n(d)$ under uncertainty scenario $\omega \in \Omega$.

At process block 110, the treatment planning system optimizes an objective function to determine a set of intensity weights for each beamlet in the proton beam configuration, wherein the objective function is calculated using the first and second dose deviations and the constraints on the tumor dose distribution is subject to a user-defined chance constraint. For example, the objective function may be defined using the following chance-constrained formulation:

$$\min \sum_{t \in T} \frac{\alpha_t}{|CTV_t|} \sum_{i \in CTV_t} |D_{ti}(\omega_0) - D_t^0| +$$

$$\sum_{n \in O} \frac{\alpha_n}{|V_n|} \sum_{i \in V_n} (D_{ni}(\omega_0) - D_n^0)^+ \text{ s.t.}$$

$$P\{L_t \leq f_t(d) \leq U_t \forall t \in T\} \geq 1 - \varepsilon \quad (1)$$

-continued $$f_n(d, \omega_0) \leq U_n \forall n \in O \quad (2)$$

$$d_j \geq 0 \forall j \in J.$$

As mentioned, $\omega_0$ denotes a nominal scenario, $CTV_t$ denotes a set of all voxels in the target volume CTV of tumor t in T, $V_n$ denotes a set of all voxels of the non-target volume organs at risk (OAR) n in a set of all OAR O, $D_t^0$ is the prescribed dose of the tumor t. $D_n^0$ is the dose constraint of OAR n, the dose received by voxel i of tumor t is denoted by $D_t$ and that received by voxel i of OAR n is denoted by $D_{ni}$, $\alpha_t$ denotes a penalty weight for the tumor t, and $\alpha_n$ denotes a penalty weight for the OAR n. The penalty weights are used in the treatment planning to indicate the importance of different structures in the clinical practice and these penalty weights can be adjusted by the treatment planners. A trial-and-error process may be used to get the optimal penalty weight values to achieve the best balance between tumor coverage and OAR protection.

In Eq. (1), $f_t(d)$ may have different values under different uncertainty scenarios. The chance constraint ensures that dose distribution requirements for tumors are satisfied with a probability P no less than $1-\varepsilon$, where P stands for the probability of the corresponding constraints to be satisfied. And $L_t$, $U_t$ are the lower and upper constraints of the tumor dose distribution, respectively. When setting $\varepsilon=0$, Eq. (1) reverts to a conventional constraint, and when setting $\varepsilon=1$, constraint Eq. (1) may be ignored. The constraints in Eq. (2) is used to control the OAR dose distribution, where $U_n$ is the upper constraint of the OAR dose distribution. The objective function of the above optimization model takes a linear form and is the weighted sum of difference values between the real doses and the prescribed doses for all voxels in tumors and organs under the nominal scenario $\omega_0$. The optimal objective value reflects the optimal plan quality achievable. In particular, smaller optimal objective value may be desirable for a better plan quality.

The form of the parameter $f_t(d)$ may play a key role in controlling the quality of the treatment plan under uncertainty. Therefore, the formula based on CVaR to implement the dose volume constraints for tumors and OARs may be adopted. For tumor $t \in T$, the abstract form $L_t \leq f_t(d) \leq U_t$ in the constraint Eq. (1) is defined as:

$$\underline{\rho}_t - \frac{1}{(1-\tau)|CTV_t|} \sum_{i \in CTV_t} (\underline{\rho}_t - D_{ti})^+ \geq \gamma_t^l D_t^0 \quad (3)$$

$$\overline{\rho}_t + \frac{1}{(1-\tau)|CTV_t|} \sum_{i \in CTV_t} (D_{ti} - \overline{\rho}_t)^+ \leq \gamma_t^h D_t^0, \quad (4)$$

where $\tau$ is used to control the percentage of the high dose volume relative to the total volume of $CTV_t$ and $\underline{\rho}_t$ and $\overline{\rho}_t$ are auxiliary variables. The constraint Eq. (3) indicates that the average dose of the subset of the target t with the percentage volume of $(1-\tau)$ receiving the lowest amount of radiation need to be at least $\gamma_t^l D_t^0$. Similarly, the constraint Eq. (4) means that the average dose of the subset of the target t with the percentage volume of $(1-\tau)$ receiving the highest amount of radiation need to be at most $\gamma_t^h D_t^0$. By setting $\gamma_t^l$ and $\gamma_t^h$ close to 1, the treatment planning system may achieve good tumor dose distribution as shown. Similarly, for organ $n \in O$, its constraint Eq. (2), $f_n(d,\omega_0) \leq U_n$ is expressed as:

$$\bar{p}_n + \frac{1}{(1-\tau)|V_n|} \sum_{i \in V_n} (D_{ni}(\omega_0) - \bar{p}_n)^+ \leq U_n^0. \quad (5)$$

$U_n^0$ may be set as the maximum dose allowed by $(1-\tau_n)$ percentage volume of OAR n.

Using the above-described optimization process that determines optimized dose distributions, at process block 112, any number of proton treatment plans may be generated. For instance, the above-described optimization process may be utilized in a planning or replanning proton treatment protocol with the user-defined tolerance level to control the balance between plan quality and plan robustness.

In addition, the treatment planning system may generate a DVH using the tolerance level and displaying the DVH in the generated report. The treatment planning system may also display the DVH indices in the generated report. The corresponding DVH indices, which are used in clinic to judge the plan quality, could be extracted from these DVH curves.

The new robust chance-constrained model is benchmarked with a PTV-based formulation. For the PTV-based formulation, which uses the same objective function as that of the robust chance-constrained model except that the tumor voxels are from the PTV of the tumor t, denoted by $PTV_t$.

$$\min \sum_{t \in T} \frac{\alpha_t}{|PTV_t|} \sum_{i \in PTV_t} |D_{ti}(\omega_0) - D_t^0| + \sum_{n \in O} \frac{\alpha_n}{|V_n|} \sum_{i \in V_n} (D_{ni}(\omega_0) - D_n^0)^+$$

The PTV is formed by uniform expansion of CTV by 3 mm for the head and neck (H&N) case and 5 mm for the lung and prostate cases. The PTV-based optimization is unconstrained. It does not consider range uncertainties and it considers setup uncertainties implicitly as they are taken into consideration by the PTV margin. The PTV-based formulation optimizes dose distribution so that the difference between target doses and actual doses of tumors and organs is minimized under the nominal scenario.

The effectiveness of the new model is benchmarked on 3 clinical cases including one prostate cancer, one lung cancer, and one H&N cancer. Table 1 lists the planning parameters of the 3 cases.

TABLE 1

Parameter Settings

| Cancer Cases | Beamlets | $D_t^0$ (Gy) | $\tau$(%) | $\gamma_t^l$ | $\gamma_t^h$ |
|---|---|---|---|---|---|
| Prostate | Beam 1: 1495 | 76 | 20 | 0.99 | 1.015 |
| | Beam 2: 1497 | | | | |
| Lung | Beam 1: 7250 | 74 | 20 | 0.99 | 1.01 |
| | Beam 2: 6075 | | | | |
| | Beam 3: 6211 | | | | |
| | Beam 4: 7164 | | | | |
| Head and neck | Beam 1: 2107 | 66 | 20 | 0.99 | 1.01 |
| | Beam 2: 1993 | | | | |
| | Beam 3: 2227 | | | | |

A discrete set $\Omega$ is used to describe the setup and range uncertainties. For the H&N and the lung cancer cases, 9 scenarios (8 perturbed plus the nominal) were obtained as follows. The interfractional patient setup uncertainties were simulated by shifting the isocenter of the patient in the anteroposterior (A-P), superior-inferior (S-I), and right-left (R-L) directions by 3 mm for the head and neck cancer case and 5 mm for the other 2 cases, yielding 6 scenarios. Range uncertainties were simulated by scaling the stopping power ratios by ±3.5% to generate 2 additional scenarios. The influence matrix for the corresponding uncertainty scenario was recalculated using a self-developed treatment planning system. For the demonstration purpose, it is assumed that the nominal scenario had the probability of 0.6 and each of these 8 uncertainty scenarios had the probability of 0.05. In this study $\varepsilon$ was set to be 0.05, therefore only one scenario was allowed to be ignored.

To demonstrate the effectiveness of the present method, 21 uncertainty scenarios (20 perturbed plus the nominal) were considered for the prostate cancer case. For each of the proton ranges (nominal, minimum, and maximum), the isocenter of the patient was rigidly shifted in the A-P, S-I, and R-L directions, respectively, yielding 18 dose distributions (6 per proton range). The other 2 were obtained from minimum and maximum proton ranges with the patient at the nominal position. Again for the demonstration purpose, here every uncertainty scenario was assumed to have a probability of 0.02. In this case $\varepsilon$ was set as 0.04, therefore 2 scenarios may be neglected. The treatment planning system generates 2 plans for each of the 3 clinical cases: one using the PTV method and the other using the robust CVaR chance-constrained treatment planning with the target as the clinical target volume (CTV). For all the 3 cases, 21 scenarios are used to evaluate the quality of a plan regardless of whether the plan is obtained by 21 scenarios (prostate cancer case) or 9 scenarios (H&N and lung cancer cases).

Dose-volume histogram (DVH) indices comparing CTV dose coverage, homogeneity, and OAR sparing are evaluated. D95% (the dose covering the highest 95% of the structure's volume) and D5% (the dose covering the highest 5% of the structure's volume) are derived from the CTV DVH. CTV D95% and D5%-D95% are used to assess CTV dose coverage and homogeneity, respectively. The lowest dose covering a percentage of the structure's volume (D %) and the percentage volume of a structure that receives at least a certain amount of dose (V) are compared for OARs, which are derived from an OAR's DVH. For the prostate cancer case, V70 of rectum and V65 and V40 of bladder were compared. For the H&N cancer case, D1% of brainstem, brain, and spine, mean doses of parotids and oral cavity were compared. For the lung cancer case, the treatment planning system uses D1% dose for the spinal cord, and V20 and mean dose of the normal lung.

To evaluate and compare IMPT plans, the treatment planning system may further use a robustness quantification technique that displays the envelope of all DVHs in band graphs of the 20 dose distributions corresponding to the scenarios of range and setup uncertainties. For convenience, the DVHs of nominal scenarios are also displayed in the robustness quantification. The nominal DVH curve is drawn by a red line. In the chance-constrained model, the DVH curves associated with the ignored scenarios are drawn by black lines. This robustness quantification technique is effective at determining an IMPT plan's sensitivity to uncertainties.

In general, chance-constrained optimizations are challenging to solve. However, it may be assumed that $\Omega$ is a finite discrete set, the treatment planning system can replace constraint Eq. (1) with the following linear constraints and convert the chance-constrained model to a solvable mixed-integer programming (MIP) problem after introducing a binary variable for each scenario:

$$L_t - Mz_\omega \leq f_t(d,\omega) \leq U_t + Mz_\omega \forall t \in T, \omega \in \Omega \quad (6)$$

$$\Sigma_{\omega \in \Omega} p_\omega z_\omega \leq \varepsilon \quad (7)$$

$$z_\omega \in \{0,1\} \forall \omega \in \Omega, \quad (8)$$

where M is a large number relative to other parameter values. Specifically, the enforcement of the constraint in scenario $\omega$ with probability $p_\omega$ is determined by the binary variable $z_\omega$. From Eq. (6), if $z_\omega=0$, the constraint has to be satisfied for w. When $z_\omega=1$, it can be ignored because of the big M. Eq. (7) is added so that the constraint Eq. (1) can be satisfied with a probability greater than or equal to $1-\varepsilon$.

In the objective function, nonlinear terms such as absolute values and Heaviside functions can be easily linearized. Therefore, the new chance-constrained IMPT planning problem may be solved using commercial solvers such as IBM CPLEX version 12.5 (Armonk, N.Y.). This process however is slow. In order to improve computational efficiency, a customized Benders decomposition algorithm is designed. Rather than considering all variables simultaneously. Benders decomposition divides the original problem into a simpler master problem, which contains only integer variables at the beginning, and a sub-problem, which only includes continuous variables. In the solution process, new constraints (i.e., Benders cuts) describing the shape of the feasible region of the sub-problem are iteratively generated and added to the master problem. The solution of the master problem will approach that of the original problem after iterations.

Table 2 shows the tumor DVH indices achieved by the robust chance-constrained method and the PTV method. To measure tumor dose coverage, the first row, entitled Nominal $D_{95\%}$ shows the $D_{95\%}$ of tumor of the nominal scenario. The second and the third row list the lowest (worst-case) and average $D_{95\%}$ of tumor among all scenarios, respectively. They represent the dose coverage of the tumor under uncertainties. The fourth to sixth row show $D_{5\%}$-$D_{95\%}$ of the nominal, largest (worst-case) $D_{5\%}$-$D_{95\%}$ and average $D_{5\%}$-$D_{95\%}$ of all scenarios, respectively. They represent the dose homogeneity of the tumor under uncertainties. In the last 3 rows, the treatment planning system chooses the width of the DVH band to quantify the plan robustness under uncertainty; it was calculated as the DVH band widths at $D_{95\%}$, $D_{50\%}$ and $D_{5\%}$.

Due to the nature of chance constraints, the unlikely and thus "ignored" scenarios are not considered in the optimization. However, the treatment planning system evaluates the generated plans' quality using all 21 scenarios (the nominal and 20 uncertain scenarios).

TABLE 2

Tumor Dose Distribution

| | Prostate | | Head and Neck | | Lung | |
|---|---|---|---|---|---|---|
| | CC | PTV | CC | PTV | CC | PTV |
| Nominal $D_{95\%}$(Gy) | 72.6 | 72.1 | 63.8 | 64.3 | 73 | 71.8 |
| Min $D_{95\%}$(Gy) | 66.1 | 57.1 | 55.9 | 53.7 | 61.1 | 58.5 |
| Avg $D_{95\%}$(Gy) | 72.4 | 67.5 | 61.8 | 60.2 | 68.6 | 67 |
| Nominal $D_{5\%}$-$D_{95\%}$(Gy) | 8.5 | 10.1 | 4.5 | 3.4 | 3.1 | 4.2 |
| Max $D_{5\%}$-$D_{95\%}$(Gy) | 14.8 | 25.2 | 14.4 | 16.2 | 16.4 | 19.1 |
| Avg $D_{5\%}$-$D_{95\%}$(Gy) | 7.9 | 16.7 | 7.5 | 11.2 | 8.7 | 12 |
| $D_{95\%}$ DVH band | 8.4 | 15 | 7.9 | 10.6 | 11.9 | 13.3 |
| $D_{50\%}$ DVH band | 1.2 | 5.4 | 0.6 | 4.4 | 0.6 | 4.8 |
| $D_{5\%}$ DVH band | 1.9 | 6.7 | 2.5 | 8.3 | 1.8 | 6.2 |

CC refers to "chance-constrained," PTV refers to a "planning target volume," Avg refers to an average, and DVH refers to a "dose-volume histogram."

Figures 2A, 2B:
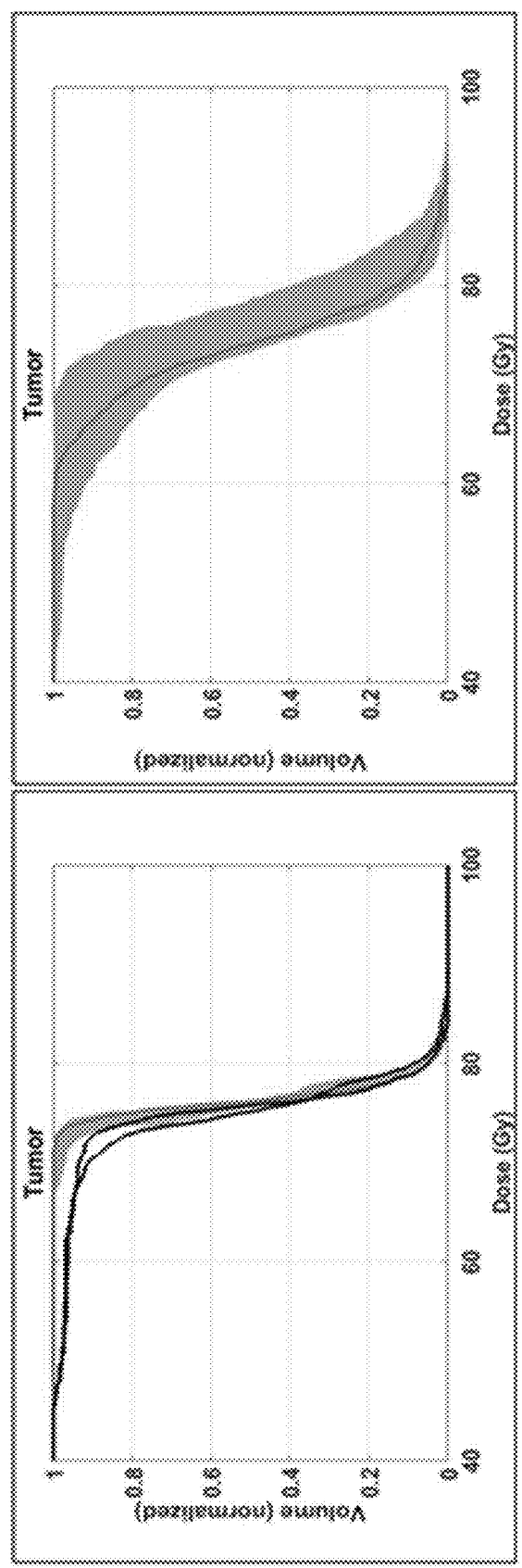
FIG. 2A illustrates tumor dose DVH for 21-scenario prostate cancer using plans of the new chance-constrained model.
FIG. 2B illustrates tumor dose DVH for 21-scenario prostate cancer using plans of PTV model.
Figures 2C, 2D:
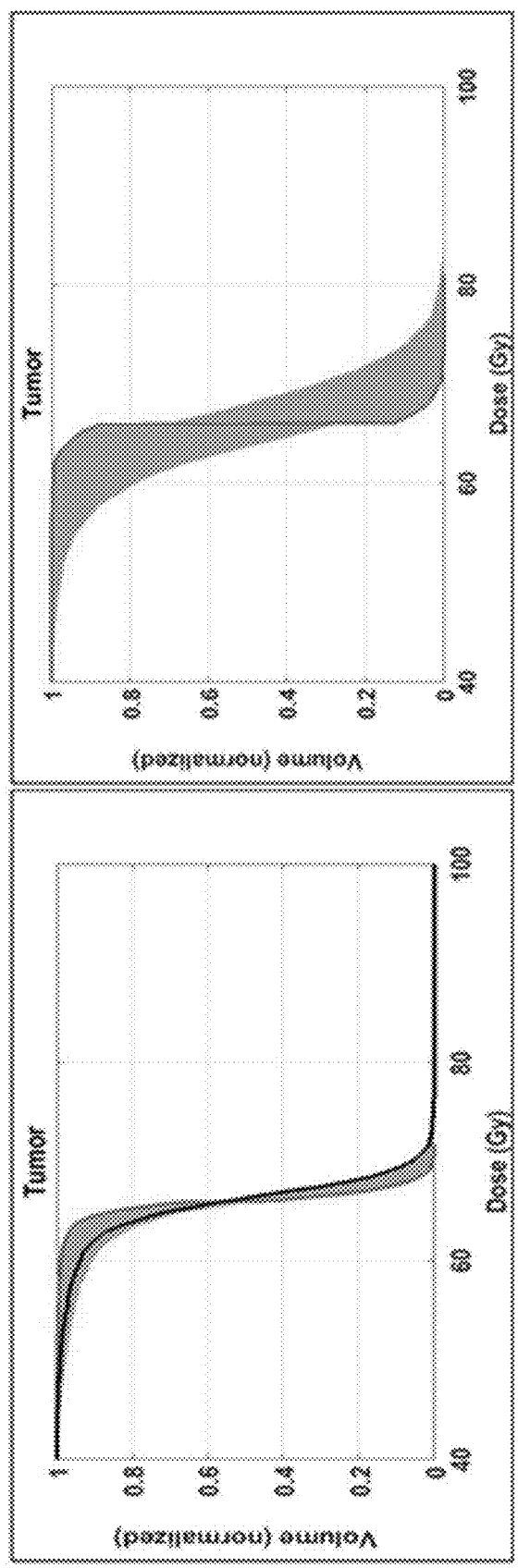
FIG. 2C illustrates tumor dose DVH for head and neck cancer using plans of the new chance-constrained model.
FIG. 2D illustrates tumor dose DVH for head and neck cancer using plans of PTV model.
Figures 2E, 2F:
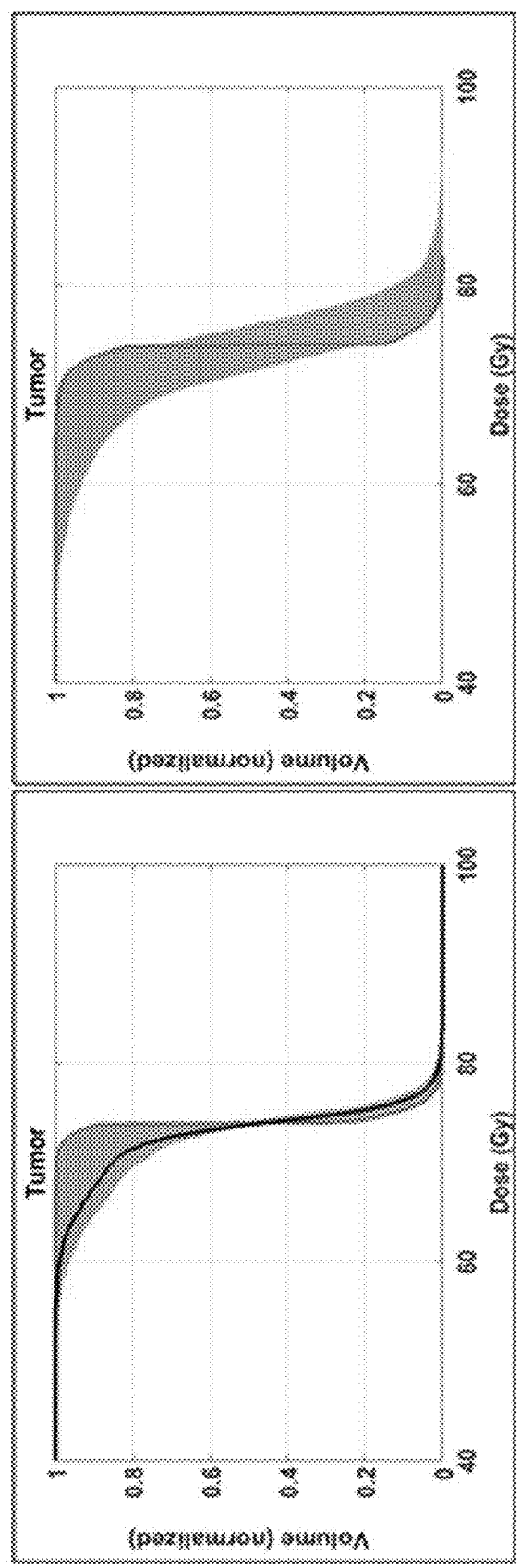
FIG. 2E illustrates tumor dose DVH for lung cancer using plans of the new chance-constrained model.
FIG. 2F illustrates tumor dose DVH for lung cancer using plans of PTV model.

FIG. 2A-2F illustrate tumor dose DVH for the 3 cases. Specifically, FIG. 2A illustrates tumor dose DVH for 21-scenario prostate cancer using plans of the new chance-constrained model. FIG. 2B illustrates tumor dose DVH for 21-scenario prostate cancer using plans of PTV model. FIG. 2C illustrates tumor dose DVH for head and neck cancer using plans of the new chance-constrained model. FIG. 2D illustrates tumor dose DVH for head and neck cancer using plans of PTV model. FIG. 2E illustrates tumor dose DVH for lung cancer using plans of the new chance-constrained model. FIG. 2F illustrates tumor dose DVH for lung cancer using plans of PTV model.

FIG. 2A-2F use the DVH bands derived from the two methods to illustrate the sensitivities of a treatment plan to uncertainties. For prostate and lung cancer cases, all quantities of $D_{95\%}$, $D_{5\%}$ $D_{95\%}$, and DVH band of the new chance-constrained model are uniformly better than those of the PTV method as graphically shown by FIGS. 2A-2B and 2E-2F. For the head and neck cancer case in FIG. 2C-2D, the plan of the chance-constrained model have slightly smaller Nominal $D_{95\%}$ and slightly bigger Nominal $D_{5\%}$-$D_{95\%}$, while all other quantities of the chance-constrained model still outperform those of the PTV method.

The OAR DVH indices for each case are listed in Table 3, which shows the values of the nominal scenario and also gives the average and the worst-case values considering all scenarios (including the ignored scenarios). For the prostate cancer and lung cancer cases, the OAR sparing may be satisfied for both the chance-constrained model and the PTV method. The chance-constrained model delivers smaller doses to all normal organs considered. For the challenging head and neck cancer case, the ipsilateral parotid had to be compromised. With the exception that the worst-case $D_{1\%}$ of brain stem is slightly higher, the chance-constrained method gives superior OAR sparing than the PTV method for all other organs.

Figure 3A:
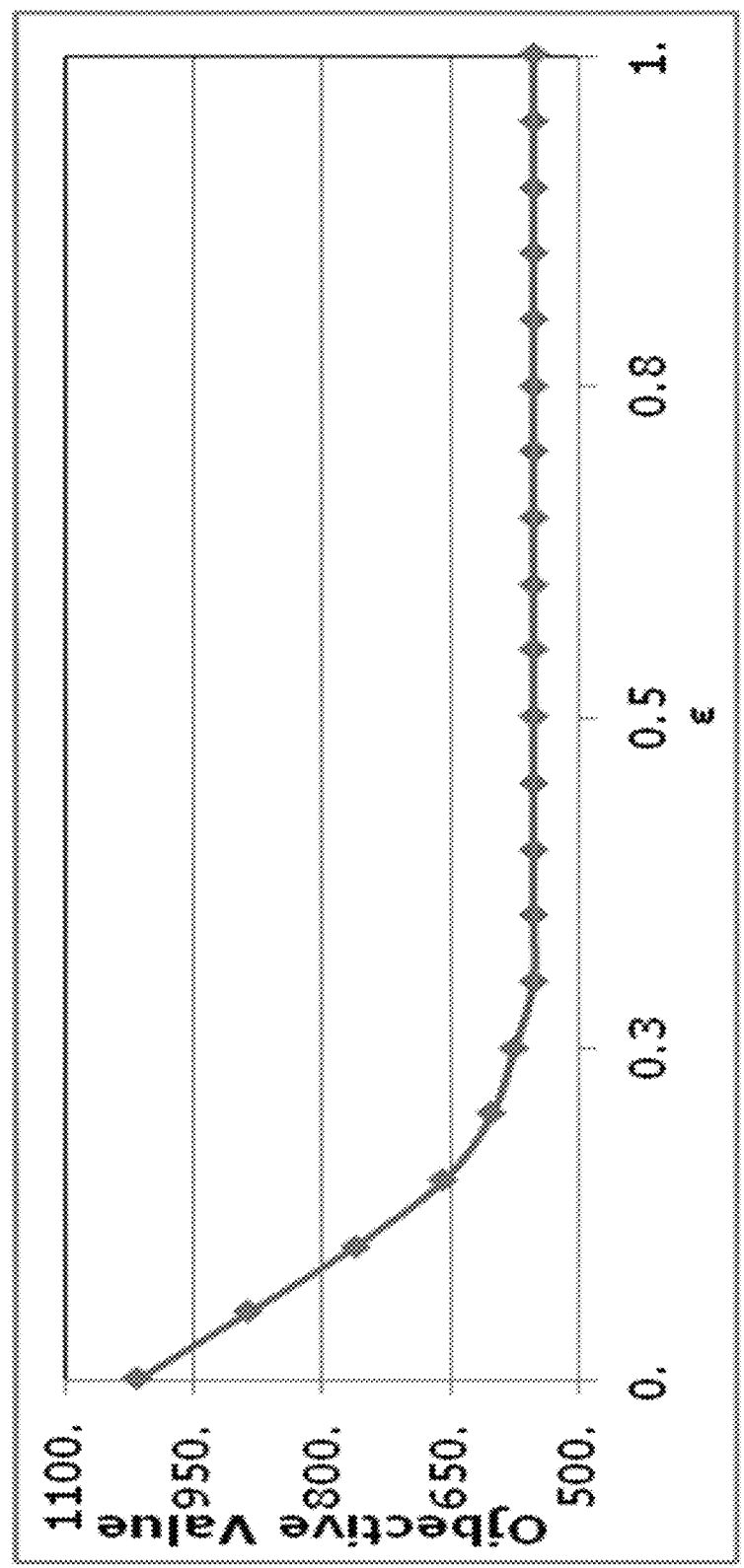
FIG. 3A shows the relationship between objective value and tolerance level $\varepsilon$.
Figure 3B:
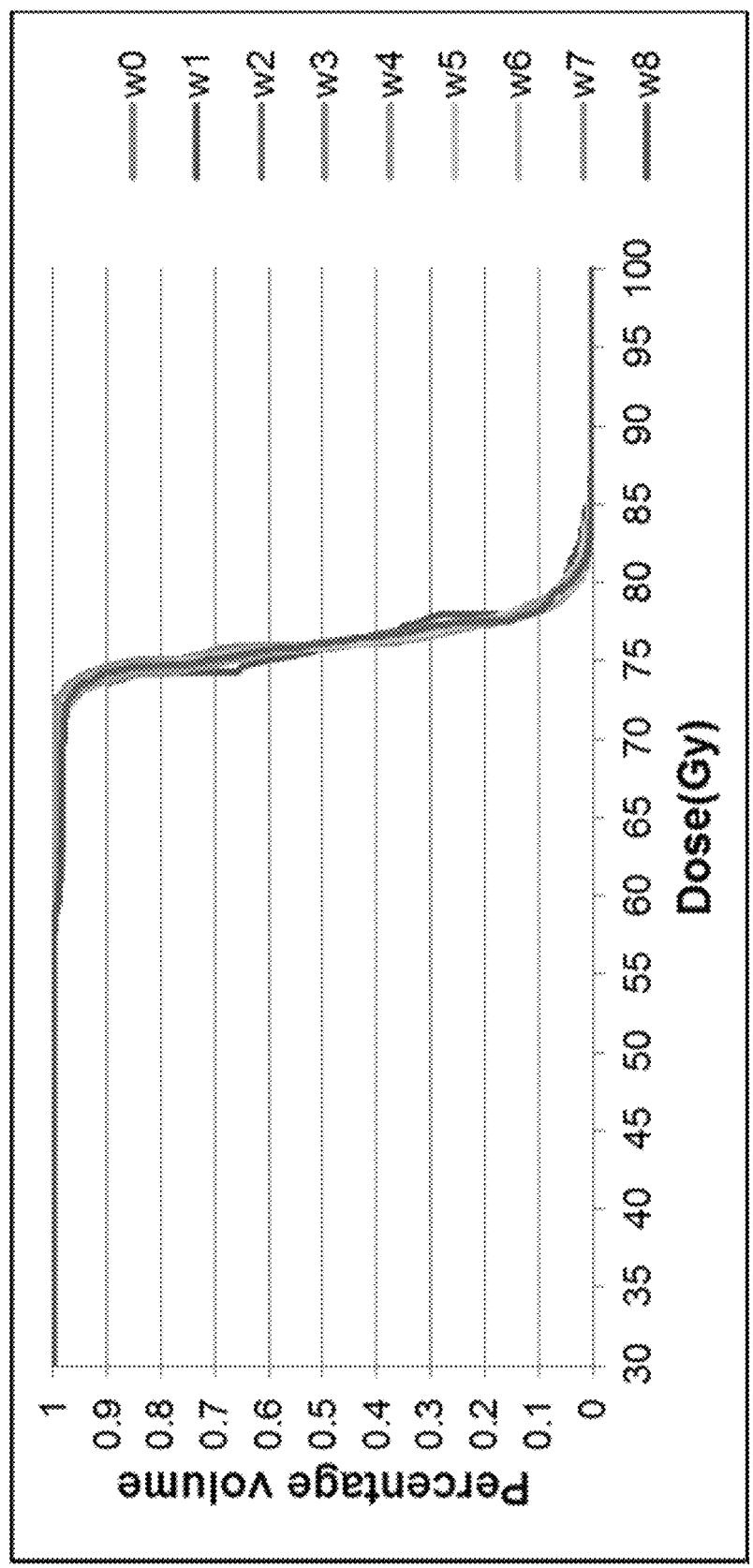
FIG. 3B shows DVH curves of the tumor for all scenarios under $\varepsilon=0$.
Figure 3C:
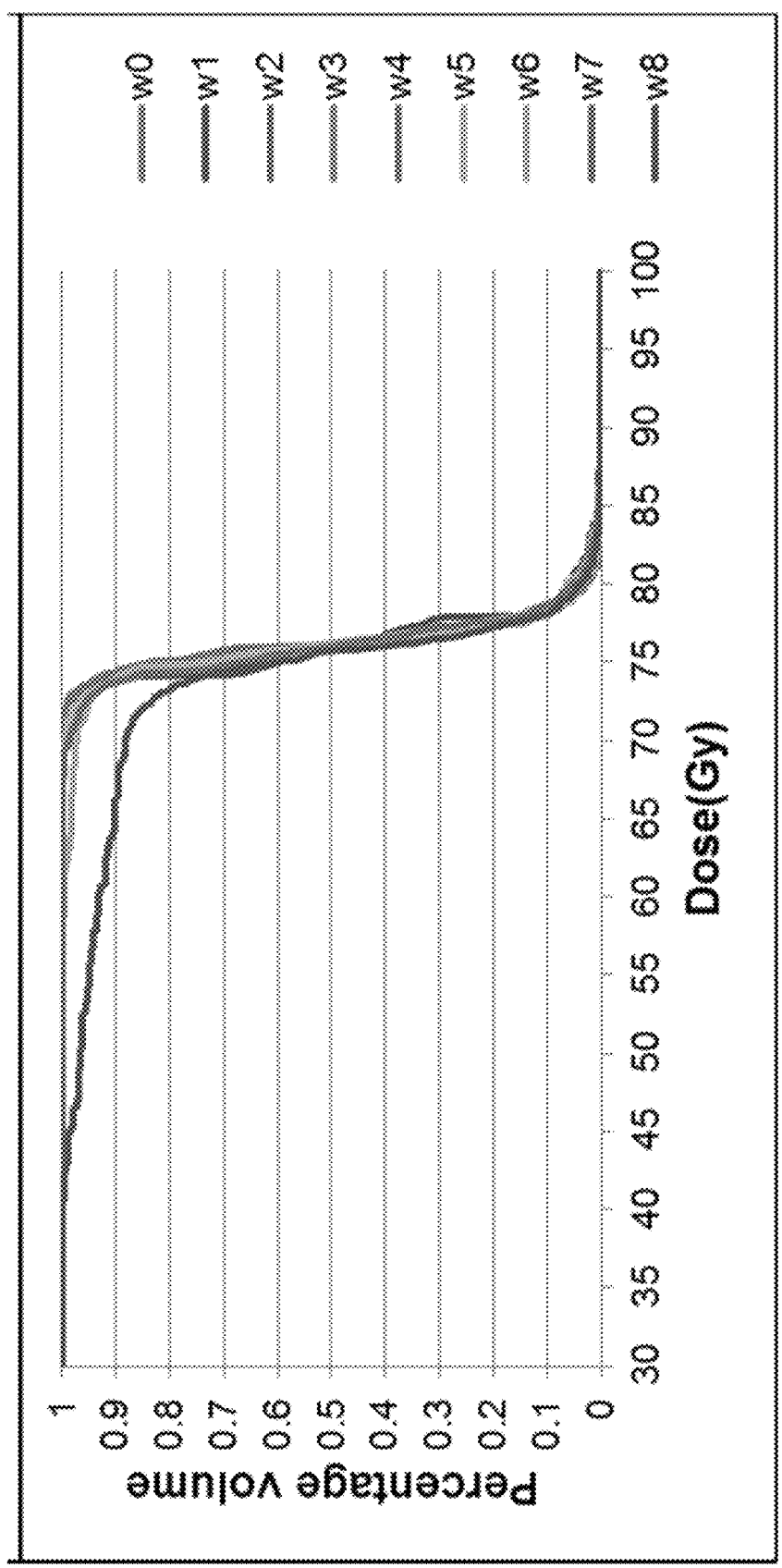
FIG. 3C shows DVH curves of the tumor for all scenarios under $\varepsilon=0.05$.

FIG. 3A shows the relationship between objective value and tolerance level $\varepsilon$. Here, the treatment planning system considers 8 scenarios. The curve is decreasing between $\varepsilon=0$ and 0.3 and purely a horizontal line between $\varepsilon=0.3$ and $\varepsilon=1.0$. The DVH curves of the tumor for all scenarios under $\varepsilon=0$ are shown in FIG. 3B. The DVH curves of the tumor for all scenarios under $\varepsilon=0.05$ are shown in FIG. 3C.

In FIG. 3A, it can be seen that relaxing the tolerance level cannot always improve the nominal plan quality, since at some point ($\varepsilon=0.3$) it will saturate. In other words, when 6 scenarios (out of 8) were allowed to be ignored, the objective value reached its lowest possible value (best plan quality). After that, the plan quality under the nominal scenario, i.e., the objective value, could not be further improved when the system further relaxes the tolerance level $\varepsilon$.

TABLE 3

| | | Dose of Organs at Risk | | | | | |
|---|---|---|---|---|---|---|---|
| | | Prostate(large) | | | Lung | | |
| | | Rectum $V_{70}$(%) | Bladder $V_{65}$(%) | Bladder $V_{40}$(%) | Spinal Cord $D_{1\%}$(Gy) | Lung $V_{20}$(%) | Lung MLD(Gy) |
| PTV | Nominal | 1.8 | 7 | 3.3 | 3.1 | 29.6 | 10.4 |
| | Average | 4.7 | 3.4 | 6.8 | 4.5 | 30.1 | 10.4 |
| | Max | 11.4 | 6.3 | 10.2 | 10.2 | 33.7 | 11.9 |
| CC | Nominal | 1.7 | 6.3 | 2.6 | 1.7 | 27.6 | 9.3 |
| | Average | 2.3 | 2.7 | 6.4 | 2.7 | 27.7 | 9.3 |
| | Max | 8.2 | 5.1 | 9.4 | 8.9 | 31.5 | 10.6 |

| | | Head and Neck | | | | | |
|---|---|---|---|---|---|---|---|
| | | Brain Stem $D_{1\%}$(Gy) | Brain $D_{1\%}$(Gy) | Spine $D_{1\%}$(Gy) | Parotid MLD(Gy) (contra-lateral) | Parotid MLD (Gy) (ipsi-lateral) | Oral Cavity MLD(Gy) |
| PTV | Nominal | 23.6 | 23 | 38.4 | 8.9 | 42.8 | 0.2 |
| | Average | 22.6 | 22.7 | 38.8 | 9.1 | 42.8 | 0.2 |
| | Max | 25.6 | 24.9 | 44.4 | 11.2 | 48.6 | 0.3 |
| CC | Nominal | 19.9 | 15.2 | 32.1 | 6.9 | 30 | 0.2 |
| | Average | 21.3 | 15.3 | 32.9 | 7 | 30.2 | 0.2 |
| | Max | 28.2 | 16.8 | 38.4 | 8.4 | 36.4 | 0.2 |

MLD refers to a "mean dose of the normal lung."

The new chance constrained model may introduce a binary variable z (thus MIP), which might greatly prolong the optimization time. For example, the solver, CPLEX version 12.5, is unable to find a solution for the lung cancer case within a reasonable time frame. As shown by Table 4, the Benders decomposition algorithm dramatically sped up the optimization compared to the commercial solver CPLEX.

The robust chance-constrained model yields clinically acceptable plans as demonstrated in the 3 clinical cases. Dose volume constraints of tumors and OARs in the presence of uncertainties are satisfied by explicitly adding CVaR chance constraints in every uncertainty scenario.

The new chance-constrained model outperforms the PTV method in terms of tumor coverage, homogeneity, and plan robustness. Even when the ignored extreme scenarios are considered, $D_{95\%}$, $D_{5\%}$-$D_{95\%}$, and the DVH bandwidths of the tumor from the disclosed model are mostly better than the results obtained using the PTV method. For the OAR sparing, the dose volume constraints are easily met by both methods for most clinical cases. However, in the challenging H&N cancer case, the disclosed method demonstrates its superiority over the PTV method by greatly improving the doses in critical organs under the nominal and perturbed scenarios. In clinical practice, the chance-constrained IMPT robust treatment planning may enhance the reliability of tumor dose distribution and hence decrease the chance of local recurrence. At the same time, improved OAR protection leads to fewer complications and better quality of life for patients.

TABLE 4

| | Computational Results | | |
|---|---|---|---|
| | Cplex | BD | |
| | Time(s) | Time(s) | Iteration |
| Prostate(21 sce) | 36660 | 18111 | 56 |
| H&N(8 sce) | 520986 | 28357 | 8 |
| Lung(8 sce) | NA | 67893 | 8 |

By introducing the adjustable tolerance level ε, the treatment planning system may flexibly ignore some extreme scenarios and avoid overly conservative plans. A small tolerance level ensures good plan robustness but may inevitably compromise the nominal plan quality given the same optimization target. The disclosure investigates the relationship between plan robustness and nominal plan quality.

The curve in FIG. 3A suggests that the disclosed method makes it possible for treatment planners to explicitly control plan robustness since the tolerance level ε is adjustable by the treatment planning system. This capability is desirable in the clinics. In addition, the DVH graph can guide treatment planners in finding the optimal balance between plan quality and plan robustness.

Figure 4:
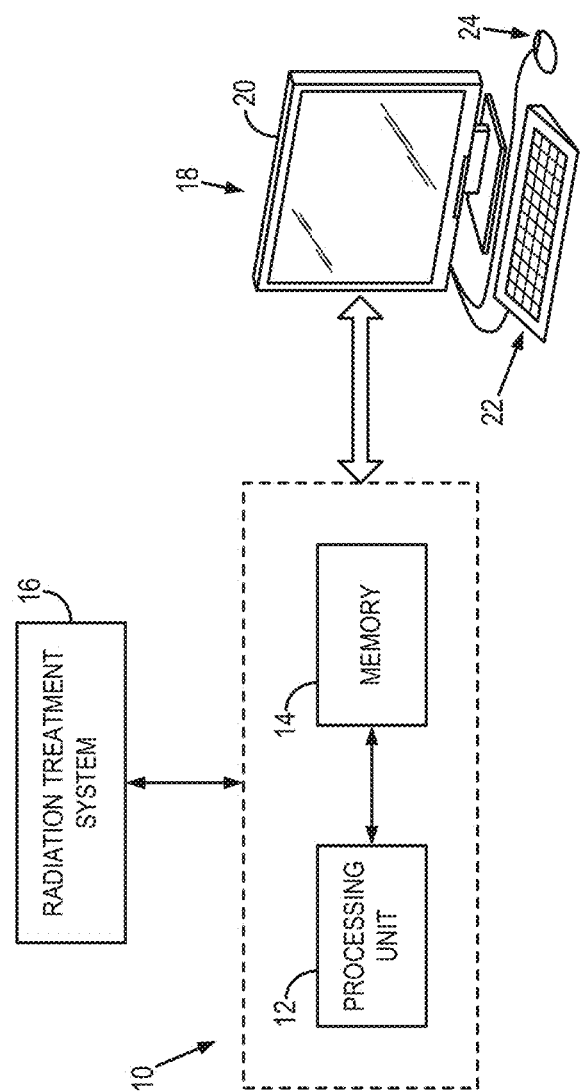
FIG. 4 is a schematic illustration of a system for use in accordance with the present disclosure.

Referring now to FIG. 4, an example of such a radiation treatment planning system 10 is illustrated. The radiation treatment planning system 10 is preferably in communication with one or more radiation treatment systems 12, which may include any suitable proton radiation treatment system.

The radiation treatment planning system 10 generally includes a memory 14 that is operably coupled to a processor unit 16. As an example, the memory 14 can include a plurality of memory elements, or can include a single memory element. In general, the memory 14 is configured to store patient data, including representations, or images acquired from patient, such as CT, MR, or PET images, as well as information related to target and non-target volumes of interest, and so on.

As an example, the processor unit 16 can be a commercially available computer processor. In addition to other processing tasks, the processor unit is configured to carry out one or more of the steps of the methods described above. In particular, to meet the challenging memory requirements and perform the specific aims efficiently for clinical utility, a hierarchical 2-level hybrid parallelization processing scheme may be configured for use with the radiation treatment planning system 10. The hierarchical hybrid parallelization scheme is composed of 2 levels of parallelization: 1) memory-distributed parallelization via message-passing interface between different computing nodes and 2) GPU-based memory-shared parallelization within one node to speed up the optimization and efficiently address the demanding memory requirement problem. This hierarchical hybrid parallelization scheme would be able to maximize the advantages and minimize the disadvantages of memory-distributed parallelization (unlimited memory, but with the bottleneck from message passing between the different nodes, which restrains the optimization speed) and GPU-based memory-shared parallelization (significantly speeding computation but with limited memory). In this manner, at least 200 times speed-up is expected, making the goal of treatment planning, say for a complicated lung case for IMPT, achievable within minutes.

In addition, preferably, the radiation treatment planning system 10 includes, or is otherwise in communication with, a user interface 18. As an example, the user interface 18 provides information to a user, such as a medical physicist. For example, the user interface 18 can include a display 20 and one or more input devices, such as a keyboard 22 and mouse 24.

In summary, the disclosure provides a method that help to control the tradeoffs between the conflicting objectives more rigorously. A quadratic objective function can penalize the errors more effectively than the linear one and has the potential to further improve the plan robustness and quality.

The disclosed robust chance-constrained IMPT planning scheme proactively hedges against the negative influence of uncertainties. The chance constraint may take the form of CVaR, which is shown to well represent the dose volume constraints in clinical practice. The model is then reformulated into a tractable MIP model that may be efficiently solved.

The treatment plan generated using the robust CVaR chance-constrained model achieved better tumor dose coverage, homogeneity, and robustness than the PTV-based planning method. In addition, OAR sparing, which is crucial in radiotherapy of cancer patients, is improved using the disclosed novel method. By studying the relationship between the tolerance level and optimal objective value, the disclosed method helps the treatment planning system to design treatment plans with a good balance between plan quality and robustness by adjusting the tolerance level.

Therefore, the present disclosure provides an approach that ensures safety and efficacy of IMPT. Using a system and method as described herein, the capabilities of radiation treatment using protons can be fully exploited, improving patient outcomes and increasing survival rate. Using the approach provided herein, it is possible to generate IMPT plans as reliable as those for photon therapy, significantly improving normal tissue sparing of IMPT. This will eliminate concerns and reluctance of practitioners to apply this highly promising treatment modality (IMPT) clinically, thus creating a far-reaching benefit for cancer patients.

The present disclosure has been described in terms of one or more preferred embodiments, and it should be appreciated that many equivalents, alternatives, variations, and modifications, aside from those expressly stated, are possible and within the scope of the disclosure.

We claim:

1. A method for generating an intensity modulated proton therapy plan, the method comprising:
   (a) obtaining, by a treatment planning system, a representation of a subject that includes information related to target and non-target volumes of interest;
   (b) obtaining, by the treatment planning system, a proton beam configuration that describes a number of beamlets and their respective arrangement;
   (c) obtaining, by the treatment planning system, a target dose distribution model in the target volumes, prescribed doses for the target volumes, and dose constraints in the non-target volumes;
   (d) computing an objective function, using the treatment planning system, the objective function having a first part with dose deviations from the prescribed doses in the target volumes, a second part with dose deviations from the dose constraints in the non-target volumes, and computing dose volume constraints for targets using a probability controlling a dose distribution in the target volumes between a lower threshold and an upper threshold;
   (e) optimizing the objective function with the treatment planning system to determine a set of intensity weights for each beamlet in the proton beam configuration, wherein the objective function is calculated using the first part and second part and the dose volume constraints; and
   (f) generating a treatment plan, executable by a proton treatment system, with the treatment planning system using the set of intensity weights determined by optimizing the objective function.

2. The method of claim 1, further comprising: receiving, using a user interface of the treatment planning system, a tolerance level ε and setting a threshold level to be 1−ε, wherein the threshold level is used to define a chance constraint ensuring that the dose distributions in the target volumes are satisfied with the probability less than the threshold level.

3. The method of claim 2, wherein the objective function minimizes a target function subject to the chance constraint on the probability, as follows:

$$\sum_{t \in T} \frac{\alpha_t}{|CTV_t|} \sum_{i \in CTV_t} |D_{ti}(\omega_0) - D_t^0| + \sum_{n \in O} \frac{\alpha_n}{|V_n|} \sum_{i \in V_n} (D_{ni}(\omega_0) - D_n^0)^+,$$

where $\omega_0$ stands for a nominal scenario, $CTV_t$ denotes a set of all voxels in a clinical target volume (CTV) of a tumor t in a set of tumors T, $V_n$ denotes a set of all voxels of in a volume of an organ at risk (OAR) n in a set of OAR O, $D_t^0$ is a prescribed dose of the tumor t, $D_n^0$ is a dose constraint of OAR n, wherein a dose received by voxel i of tumor t is denoted by $D_{ti}$, a dose received by voxel i of OAR n is denoted by $D_{ni}$, $\alpha_t$ denotes a penalty weight for the tumor t, and $\alpha_n$ denotes a penalty weight for the OAR n.

4. The method of claim 3, wherein the objective function minimizes the target function subject to a constraint of dose distribution in all OAR that is defined by:

$$f_n(d,\omega_0) \le U_n \forall n \in O,$$

where $f_n(d,\omega_0)$ is a value $f_n(d)$ under an uncertainty scenario $\omega_0 \in \Omega$.

5. The method of claim 1, further comprising:
   obtaining one or more model parameters for the dose distribution model based on at least one image acquired using one of x-ray computed tomography ("CT"), magnetic resonance imaging ("MRI"), positron emission tomography ("PET"), or proton CT.

6. The method of claim 1, wherein the method further comprises computing the objective function under a plurality of uncertainty scenarios comprising a combination of a series of setup uncertainty scenarios, a series of proton range uncertainty scenarios, and a series of motion uncertainty scenarios.

7. The method of claim 1, wherein a chance constraint on the probability is defined according to:

$$P\{L_t \leq f_1(d) \leq U_t, \forall t \in T\} \geq 1-\varepsilon,$$

where $f_t(d)$ is a parameter describing a tumor dose distribution of tumor t, $L_t$ is a lower constraint of the tumor dose distribution, $U_t$ is an upper constraint of the tumor dose distribution, T denotes a set of all tumors, and s is a tolerance level.

8. The method of claim 1, further comprising generating a report that indicates a tolerance level of the treatment plan.

9. The method of claim 8, wherein generating the report includes generating a Dose-volume histogram (DVH) using the tolerance level and displaying the DVH in the generated report.

10. The method of claim 1, wherein the method further comprises generating a report comprising one or more Dose-volume histograms (DVHs) and displaying indices corresponding to the DVHs in the generated report.

11. A treatment planning system for use in intensity-modulated proton therapy, comprising:
a memory for storing thereon a representation of a subject and a proton beam configuration, wherein the representation of the subject includes information related to target and non-target volumes of interest and the proton beam configuration describes a number of beamlets and their respective arrangement;
a processor configured for receiving the representation of the subject and the proton beam configuration from the memory and for generating a treatment plan based on the representation of the subject and the proton beam configuration;
a display for displaying the treatment plan; and
wherein the processor is configured to generate the treatment plan by:
obtaining a target dose distribution model in the target volumes, prescribed doses of the target volumes, and dose constraints in the non-target volumes;
computing an objective function, using the treatment planning system, the objective function having a first part with dose deviations from the prescribed doses in the target volumes, a second part with dose deviations from the dose constraints in the non-target volumes, and computing dose volume constraints for targets using a probability controlling a dose distribution in the target volumes between a lower threshold and an upper threshold; and
generating the treatment plan executable by a proton treatment system by optimizing the objective function to determine a set of intensity weights for each beamlet in the proton beam configuration.

12. The treatment planning system of claim 11, wherein the processor is further configured to receive, using a user interface of the treatment planning system, a tolerance level ε and set a threshold level to be 1−ε, wherein the threshold level is used by the processor to define a chance constraint ensuring that the dose distribution in the target volumes are satisfied with the probability not less than the threshold level.

13. The treatment planning system of claim 11, wherein the treatment planning system obtains one or more model parameters for the dose distribution model based on at least one image acquired using one of x-ray computed tomography ("CT"), magnetic resonance imaging ("MRI"), positron emission tomography ("PET"), or proton CT.

14. The treatment planning system of claim 11, wherein the processor is further configured to define a chance constraint on the probability according to:

$$P\{L_t \leq f_1(d) \leq U_t, \forall t \in T\} \geq 1-\varepsilon,$$

where $f_t(d)$ is a parameter describing a tumor dose distribution of a tumor t, $L_t$ is a lower constraint of the tumor dose distribution, $U_t$ is an upper constraint of the tumor dose distribution, T denotes a set of all tumors, and ε is a tolerance level.

15. The treatment planning system of claim 14, wherein the objective function minimizes a target function subject to the tolerance constraint on the probability, as follows:

$$\sum_{t \in T} \frac{\alpha_t}{|CTV_t|} \sum_{i \in CTV_t} |D_{ti}(\omega_0) - D_t^0| + \sum_{n \in O} \frac{\alpha_n}{|V_n|} \sum_{i \in V_n} (D_{ni}(\omega_0) - D_n^0)^+,$$

where $\omega_0$ stands for a nominal scenario, $CTV_t$ denotes a set of all voxels in a clinical target volume (CTV) of a tumor t in a set of tumors T, $V_n$ denotes a set of all voxels of in a volume of an organ at risk (OAR) n in a set of OAR O, $D_t^0$ is a prescribed dose of the tumor t, $D_n^0$ is a dose constraint of OAR n, wherein a dose received by voxel i of tumor t is denoted by $D_{ti}$, the dose received by voxel i of OAR n is denoted by $D_{ni}$, $\alpha_t$ denotes a penalty weight for the tumor t, and $\alpha_n$ denotes a penalty weight for the OAR n.

16. The treatment planning system of claim 15, wherein the objective function minimizes the target function subject to a constraint of dose distribution in all OAR that is defined by:

$$f_n(d,\omega_0) \leq U_n, \forall n \in O,$$

where $f_n(d,\omega_0)$ is a value $f_n(d)$ under an uncertainty scenario $\omega_0 \in \Omega$.

17. The treatment planning system of claim 14, wherein the processor is further configured to generate a report that indicates a tolerance level of the treatment plan.

18. The treatment planning system of claim 17, wherein the processor is further configured to generate a Dose-volume histogram (DVH), and display the DVH in the generated report.

19. The treatment planning system of claim 14, wherein the processor is further configured to generate a report comprising one or more Dose-volume histograms (DVHs), and display indices corresponding to the DVHs in the generated report.

20. A method for generating an intensity modulated proton therapy plan amenable to uncertainties, the method comprising:
(a) obtaining, by a treatment planning system, a representation of a subject that includes information related to target and non-target volumes of interest (VOIs);
(b) obtaining, by the treatment planning system, a proton beam configuration that describes a number of beamlets and their respective arrangement;
(c) obtaining, by the treatment planning system, a target dose distribution model in the target VOIs, prescribed doses for the target VOIs, and dose constraints for the non-target VOIs;
(d) computing dose volume constraints for the target VOIs using a selectable parameter controlling a probability for a dose distribution in the target VOIs to be between a lower threshold and an upper threshold;
(e) optimizing an objective function with the treatment planning system to determine a set of intensity weights for each beamlet in the proton beam configuration, wherein the objective function is calculated using dose deviations from the prescribed doses in the target VOIs, dose deviations from the dose constraints in the non-target VOIs, and the dose volume constraints for the target VOIs; and (f) generating a treatment plan, executable by a proton treatment system, with the treatment planning system using the intensity weights determined by optimizing the objective function.

* * * * *

UNITED STATES PATENT AND TRADEMARK OFFICE
CERTIFICATE OF CORRECTION

PATENT NO. : 10,328,282 B2  
APPLICATION NO. : 15/209699  
DATED : June 25, 2019  
INVENTOR(S) : Yu An, Jianming Liang and Wei Liu Page 1 of 2

It is certified that error appears in the above-identified patent and that said Letters Patent is hereby corrected as shown below:

In the Specification

Column 7, Line 12, " $\sum_{t \in T} \frac{\alpha_t}{|CTV_t|} \sum_{i \in CTV_t} |D_{ti}(\omega_0) - D_t^0|$ " should be -- $\sum_{t \in T} \frac{\alpha_t}{|CTV_t|} \sum_{i \in CTV_t} |D_{ti}(\omega_0) - D_t^0|$ --.

Column 7, Line 20, " $\sum_{n \in O} \frac{\alpha_n}{|V_n|} \sum_{i \in V_n} (D_{ni}(\omega_0) - D_n^o)^+$ " should be -- $\sum_{n \in O} \frac{\alpha_n}{|V_n|} \sum_{i \in V_n} (D_{ni}(\omega_0) - D_n^o)^+$ --.

Column 7, Line 60,

" $\min \sum_{t \in T} \frac{\alpha_t}{|CTV_t|} \sum_{i \in CTVt} (D_{ti}(\omega_0) - D_n^o) + \sum_{n \in O} \frac{\alpha_n}{|V_n|} \sum_{i \in V_n} (D_{ni}(\omega_0) - D_n^0)^+ s.t.$ "

should be -- $\min \sum_{t \in T} \frac{\alpha_t}{|CTV_t|} \sum_{i \in CTVt} (D_{ti}(\omega_0) - D_n^o) + \sum_{n \in O} \frac{\alpha_n}{|V_n|} \sum_{i \in V_n} (D_{ni}(\omega_0) - D_n^0)^+ s.t.$ --.

Signed and Sealed this  
Third Day of March, 2020

Andrei Iancu  
*Director of the United States Patent and Trademark Office*

Column 8, Eq. (3), " $\underline{\rho}_t - \frac{1}{(1-\tau)|(CTV_t)} \sum_{i \in CTV_t} (\underline{\rho}_t - D_{ti})^+ \geq \gamma_t^l D_t^0$ " should be
-- $\underline{\rho}_t - \frac{1}{(1-\tau)|(CTV_t)} \sum_{i \in CTV_t} (\underline{\rho}_t - D_{ti})^+ \geq \gamma_t^l D_t^0$ --.

Column 8, Eq. (4), " $\bar{\rho}_t + \frac{1}{(1-\tau)|CTV_t} \sum_{i \in CTV_t} (D_{ti} - \bar{\rho}_t)^+ \leq \gamma_t^h D_t^0$ " should be
-- $\bar{\rho}_t + \frac{1}{(1-\tau)|CTV_t} \sum_{i \in CTV_t} (D_{ti} - \bar{\rho}_t)^+ \leq \gamma_t^h D_t^0$ --.

Column 9, Eq. (5), " $\bar{\rho}_t + \frac{1}{(1-\tau)|V_n|} \sum_{i \in V_n} (D_{ni}(\omega_0) - \bar{\rho}_n)^+ \leq U_n^0$ " should be
-- $\bar{\rho}_t + \frac{1}{(1-\tau)|V_n|} \sum_{i \in V_n} (D_{ni}(\omega_0) - \bar{\rho}_n)^+ \leq U_t^0$ --.

In the Claims

Column 16, Claim 2, Line 29, "probability less" should be --probability not less--.

Column 17, Claim 7, Line 6, "of tumor" should be --of a tumor--.

Column 17, Claim 7, Line 8, (approx.), "ands" should be --and ε--.